United States Patent [19]

Moloy

[11] 4,297,748

[45] Nov. 3, 1981

[54] MIDDLE EAR BALLOON

[76] Inventor: Peter J. Moloy, 29 Cypress Way, Rolling Hills Estates, Calif. 90274

[21] Appl. No.: 109,161

[22] Filed: Jan. 2, 1980

[51] Int. Cl.³ .............................................. A61F 1/00
[52] U.S. Cl. ................................................ 3/1
[58] Field of Search ...................................... 3/1

[56] References Cited

U.S. PATENT DOCUMENTS 1,045,917  12/1912  Valiquet ............................ 3/1 UX
3,875,595  4/1975  Froning ............................... 3/1

Primary Examiner—Clifford D. Crowder
Attorney, Agent, or Firm—William W. Haefliger

[57] ABSTRACT

A device adapted to be implanted in the middle ear to block displacement of a tympanic membrane toward the round window membrane comprises:
(a) a resiliently yieldable pillow,
(b) the pillow having external configuration adapted to fit within the natural hollow of the hypotympanum.

12 Claims, 11 Drawing Figures

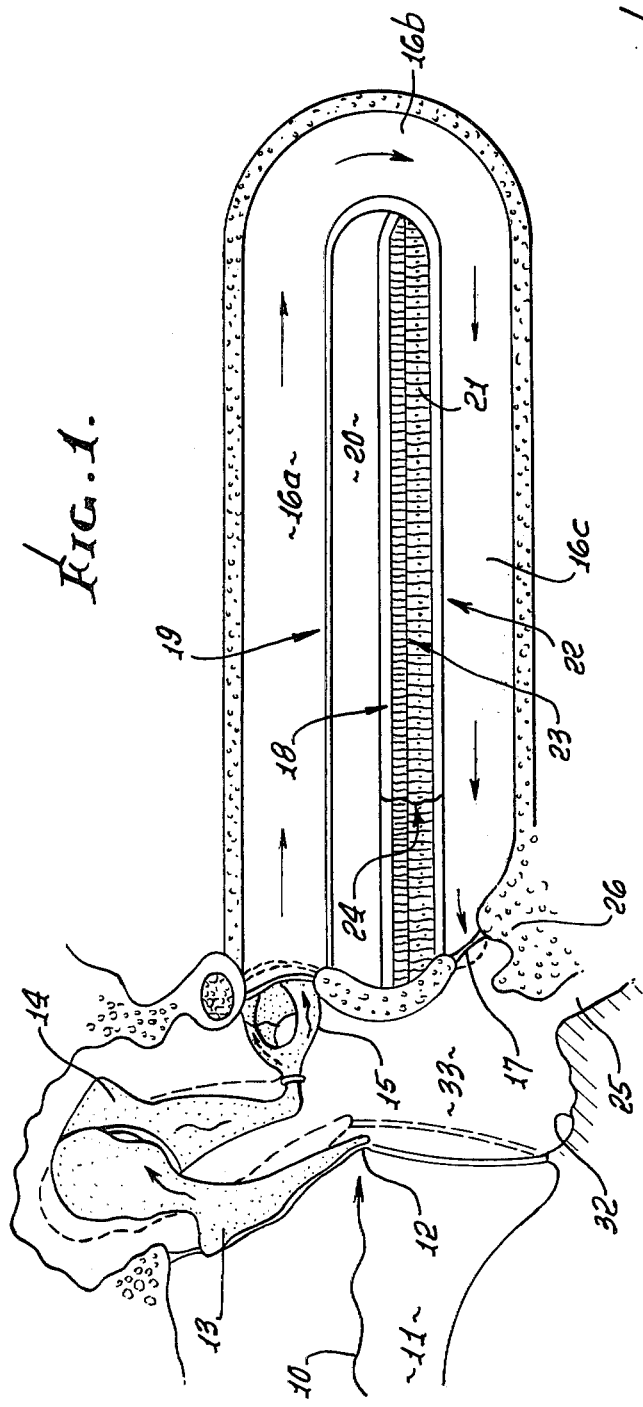
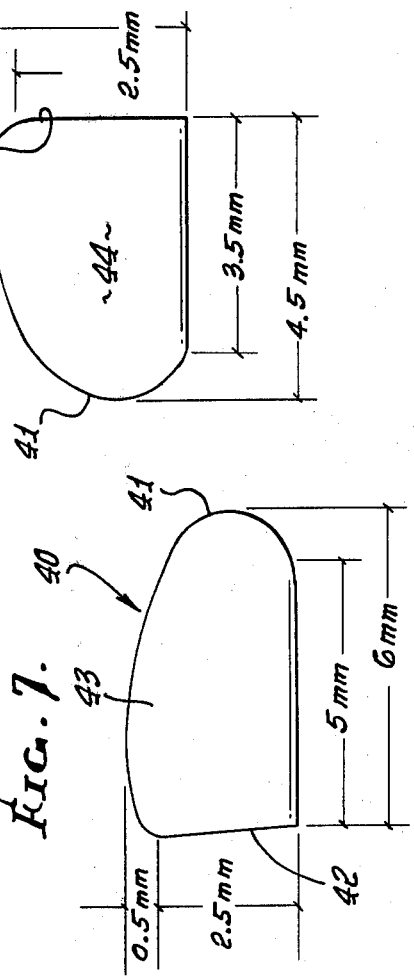
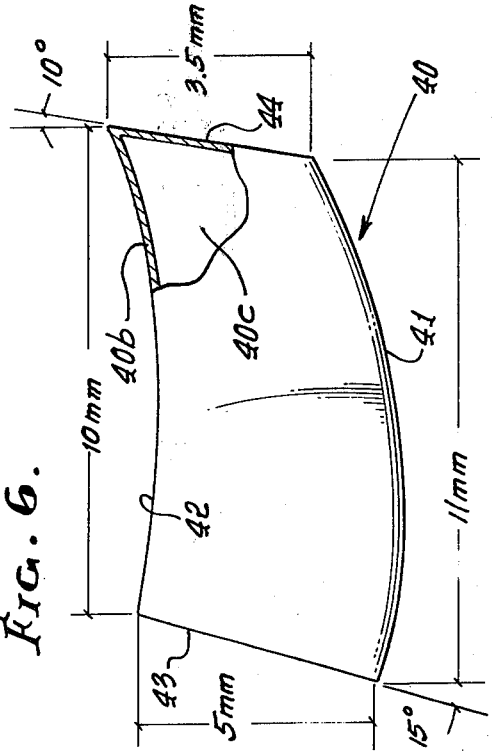

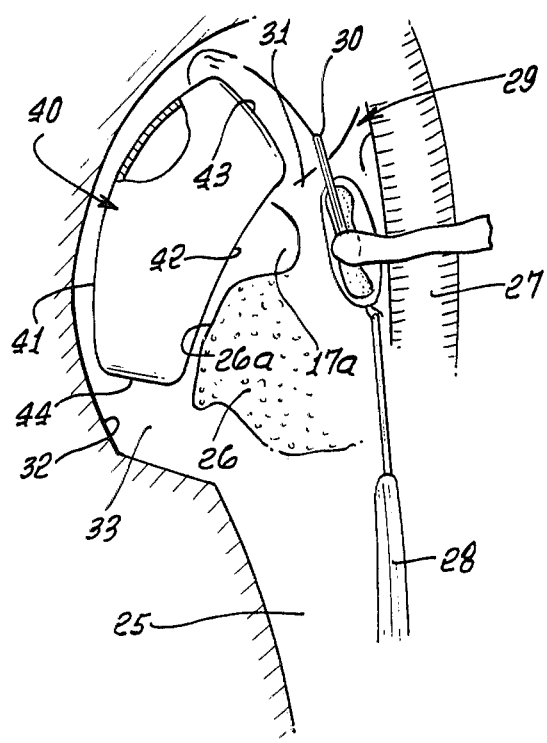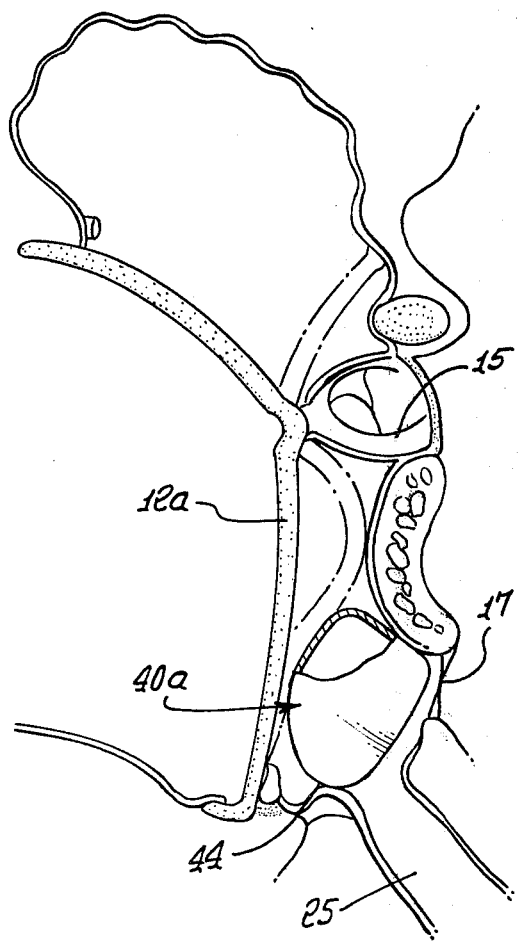

MIDDLE EAR BALLOON

BACKGROUND OF THE INVENTION

This invention relates generally to resolution of certain problems arising in connection with ear reconstruction; more specifically it concerns the provision of a device implanted in the natural hollow of the hypotympanum to improve hearing, typically under circumstances where ossicles are not intact, but also of use in situation where ossicles are intact.

Within the last twenty-five years various microsurgical concepts and procedures have evolved in efforts to solve the problems of reconstruction arising in ears operated upon for chronic middle ear disease. It is found that the results of a given techique are initially good, but deterioration often occurs as a result of post-operative wound healing, including the formation of scar tissue that blocks hearing functions.

It can be said that results cannot be predicted with accuracy due to the existence of many variables in a given ear. These include, but are not limited to: Eustachian tube function; degree of operative trauma; anatomic variation among microstructures; differences in patient healing characteristics; amount and quality of remaining mucosa; osteitis remaining, if any, after surgery; and obscure factors such as patient's immune status, ear and pharyngeal flora, and minutiae of operative techniques such as presence of talc in wound and sterile techniques. Perhaps the most important variable is the degree of interaction of these listed variables. In the past, solid devices have been temporarily employed in the middle ear; however such devices are not entirely satisfactory.

SUMMARY OF THE INVENTION

It is a major object of the invention to provide a soft, sac-like device or pillow that is permanently implantable in the hollow of the hypotympanum, typically between the ear drum or tympanic membrane and the round window membrane, so as to block the approach of the tympanic membrane into close proximity to the round window membrane. The pillow or sac is typically implanted under circumstances where the ossicles are not intact, i.e. have been or are surgically removed, techniques known as tympanoplasty III or IV; however, the pillow can also be used when the ossicles are intact, as in tympanoplasty I.

In this regard, the purpose of such sac implantation is to maintain desired functions of the middle ear, including impedance matching (known as IM), and production of desired acoustic phase differences (known as PD) between the round window and oval window, as will later appear. IM overcomes differences in density between air and water, and PD permits a traveling wave to be established in the cochlea. Type IV tympanoplasty with good resulting PD can produce 25-30 dB levels. As will be seen, the sac or pillow is typically soft and pliable, air or gas filled, and partially inflated. It is sized to remain implanted in place yet capable of changing shape in response to forces of change (i.e. due to healing) in the post-operative ear. It also resists perforation, and is easily installable.

Due to its soft, pliable character, the pillow or sac prevents undesired interference with the motion of the round window membrane by motion of the tympanic membrane, despite its location between those membranes.

These and other objects and advantages of the invention, as well as the details of an illustrative embodiment, will be more fully understood from the following specification and drawings, in which:

DRAWING DESCRIPTION

FIG. 1 is a section showing tympanocochlear relationships;

FIG. 2 is a section illustrating relationships of the medial or inner wall of the middle ear cleft to the invention;

FIG. 3 is a section showing the ear canal, and after surgical removal of certain bones;

FIGS. 6-8 show different views of the device in accordance with the invention.

DETAILED DESCRIPTION

Figure 4:
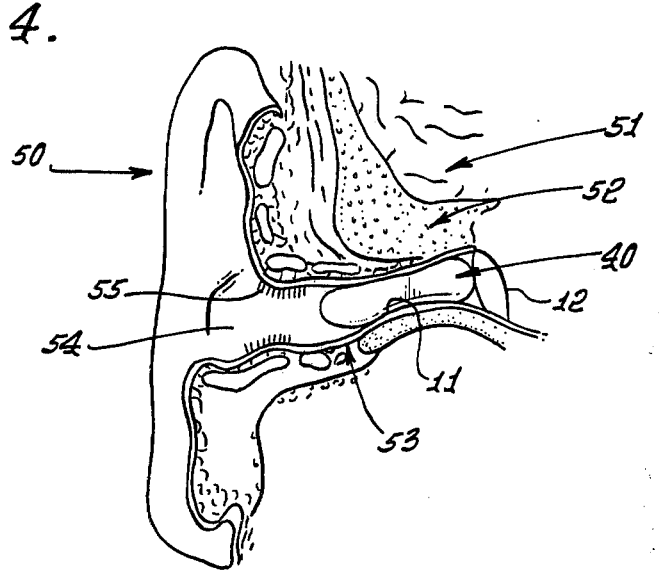
FIG. 4 is a frontal view, in section, showing the auricle and external auditory canal, with the invention employed in the latter.

In FIG. 1, sound waves, indicated by arrow 10, travel within the external auditory canal 11 to impinge upon the tympanic membrane or ear drum 12. Motion is transmitted from the latter via bone elements 13 and 14 to the stapes 15. Motion is transmitted from the stapes via the perilymph scala vestibuli 16a, helicotreme 16b and perilymph scale tympani 16c to the round window membrane 17. Additional elements are: tectorial membrane 18; Reissners membrane 19; cochlear duct 20; hair cells 21; basilar membrane 22, cilia 23; Organ of Corti 24; Eustachian tube 25, promontory 26, and hypotympanum recess 33. Referring to FIG. 2, additional elements include round window recess 17a; canal 27 of facial nerve; tendon 28 of tensor tympani muscle; ponticulus 29; tendon 30 of stapedial muscle; subiculum 31; and bony annulus 32.

In accordance with the invention, a device is adapted to be implanted in the middle ear to block displacement of the tympanic membrane to undesired extent toward the round window, thereby to preserve the phase difference between the oval window and round window. Accordingly, the motion of the round window membrane due to sound wave transmission thereto via the elements 16a, 16b and 16c is then not subjected to undesired interference by relatively out-of-phase motion.

One such device is shown at 40 FIG. 2, and at 40a in FIG. 3 wherein it is somewhat deformed by a tympanic membrane such as an artificial ear drum 12a. The device in the form of a resiliently yieldable pillow or sac, has a convex side wall 41, a concave side wall 42, substantially flat end walls 43 and 44 as best seen in FIGS. 6-8.

Convex side wall 41 is shaped to conform generally to the curvature of bony annulus 32, and concave side wall 42 conforms to the outer surface 26a of promontory 26, as is clear from FIG. 2. Therefore, the sac remains in place. In FIG. 3, it is clear that the sac or pillow 40 is located between tympanic membrane 12a and round window 17. Membrane 12a directly activates stapes 15 due to surgical reconstruction. Were it not for the blocking function of pillow 40a, the membrane 12a could at least at times approach into proximity to the round window 17 to interfere with motion thereof. The sac in FIG. 3 has rounded side wall 43 or 44 (depending on orientation of the device) closest to Eustachian tube 25.

Approximate dimensions of the sac or pillow are applied to FIG. 8, and show that the device is typically no longer than about 10 mm; also its maximum width is not greater than about 5 mm. The sac wall 40b may for example consist of silastic or other suitable plastic material, and the interior 40c may be partly inflated with a gas such as nitrogen or air. Such partial inflation insures that the sac will readily deform or deflect so as not to transmit acoustic waves from the tympanic membrane (as at 12a in FIG. 3) to the round window; i.e. the sac acoustically "decouples" the membrane 12a and the round window. At the same time, it does not prevent acoustic wave transmission from the membrane 12a to stapes 15 and the elements 16a, 16b and 16c as shown in FIG. 1. The sac may have modified shapes to fit different ear anatomies all within the purview of the invention.

Figure 5A:
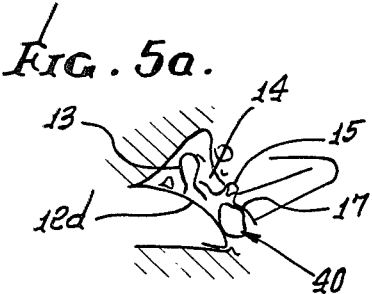
FIGS. 5a-5d are diagrams showing types of tympanoplasty with the invention employed in same.
Figure 5B:
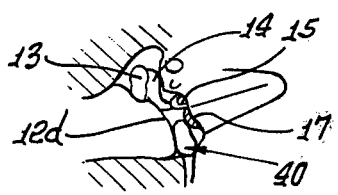
Figure 5C:
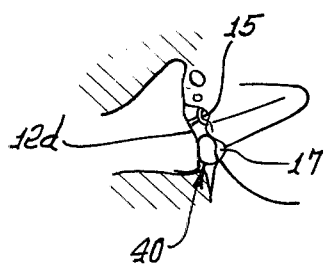
Figure 5D:
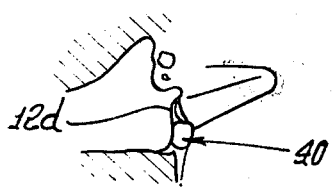

FIGS. 5a–5d show various uses of the sac or pillow 40. In FIGS. 5a and 5d the sac is used between the tympanic membrane 12d and the round window 17, with the bony elements 13–15 remaining in the ear; in FIG. 5a elements 13 and 14 have been removed; and in FIG. 5d elements 13–15 have been removed.

In FIG. 4 the modified sac 40 is shown to have another use, i.e. protective implantation in the external auditory canal, outwardly of the tympanic membrane 12. Other ear elements shown include the auricle 50; temporal lobe 51; mastoid air cells 52; ceruminous glands and ducts 53; cantilaginous canal 54; and hairs 55.

It is anticipated that other modified forms of the sac will find other uses in reconstructive ear surgery.

Note in FIG. 3 that the pillow 40a is out of contact with the round window membrane.

I claim:

1. The method of reducing blockage of air wave induced motion of the round window membrane in the inner ear, and employing a pillow, that includes
   (a) sizing the pillow for reception in the hypotympanum recess, and
   (b) implanting the pillow in said recess in a location to yieldably block displacement of the tympanic membrane toward the round window membrane, thereby to prevent undesired interference with motion of the round window membrane by motion of the tympanic membrane.

2. The method of claim 1 that includes forming said pillow as a sac and to contain a gas or gasses.

3. The method of claim 2 wherein the gas in said sac consists of air.

4. The method of claim 1 that includes the step of locating said pillow directly between a tympanic membrane and a round window membrane, but without contacting the round window membrane to block the approach of the tympanic membrane into close proximity to said round window membrane.

5. The method of claim 1 wherein the pillow is resiliently yieldable, said implanting causing the pillow to resiliently yield.

6. A device adapted to be implanted in the middle ear to block displacement of a tympanic membrane toward the round window membrane, comprising
   (a) a pillow,
   (b) the pillow having external configuration adapted to fit within the natural hollow of the hypotympanum, the pillow being elongated and having one elongated side that is outwardly convex and an opposite elongated side that is outwardly concave.

7. The device of claim 6 wherein said pillow comprises a sac containing a gas.

8. The device of claim 7 wherein the gas consists of air.

9. The device of claim 6 wherein the pillow overall length dimension along said convex side is about 11 millimeters, and the maximum width dimension between said elongated sides is about 5 millimeters.

10. The device of claim 6 wherein the pillow is resiliently yieldable.

11. The structure that includes
    (a) an elongated pillow adapted for implantation in the middle ear between the tympanic membrane and the round window membrane to yieldably block displacement of the tympanic membrane toward the round window membrane,
    (b) the pillow sized to be out of contact with the round window membrane and to be located to prevent undesired interference with the motion of the round window membrane by motion of the tympanic membrane.

12. The structure of claim 11 wherein the pillow has a convex side adapted to face said tympanic membrane to be engaged thereby.

* * * * *